US006096867A

United States Patent [19]

Byass et al.

[11] Patent Number: 6,096,867

[45] Date of Patent: Aug. 1, 2000

[54] FROZEN FOOD PRODUCT

[75] Inventors: Louise Jane Byass, Heslington; Donald Frank Darling, Colworth; Charlotte Juliette Doucet, Heslington; Richard Anthony Fenn, Colworth; Peter John Lillford, Colworth; Andrew John McArthur, Colworth; David Needham, Colworth; Christopher Sidebottom, Colworth; Keith Smallwood, Colworth; Margaret Felicia Smallwood, Heslington, all of United Kingdom

[73] Assignee: Good Humor-Breyers Ice Cream, Division of Conopco, Inc., Green Bay, Wis.

[21] Appl. No.: 08/898,351

[22] Filed: Jul. 22, 1997

[30] Foreign Application Priority Data

| | | | |
|---|---|---|---|
| Jul. 6, 1996 | [EP] | European Pat. Off. .............. | 96305499 |
| Jul. 16, 1996 | [EP] | European Pat. Off. .............. | 96305497 |
| Nov. 19, 1996 | [EP] | European Pat. Off. .............. | 96308362 |
| Mar. 14, 1997 | [EP] | European Pat. Off. .............. | 97301719 |
| Mar. 14, 1997 | [EP] | European Pat. Off. .............. | 97301733 |

[51] Int. Cl.[7] ............................ C07K 1/00; C07K 14/00; A23B 7/10

[52] U.S. Cl. .......................... 530/350; 530/326; 530/328; 530/300; 426/100; 426/101; 426/49; 426/656; 426/660; 426/139

[58] Field of Search .................................... 530/300, 350, 530/326, 328; 514/12; 426/565, 100, 101, 103, 139, 656, 660, 521, 524, 49

[56] References Cited

U.S. PATENT DOCUMENTS 5,194,269 3/1993 Lee ........................................... 426/61

FOREIGN PATENT DOCUMENTS 9222581 12/1992 WIPO .
9639878 12/1996 WIPO .

*Primary Examiner*—Avis M. Davenport
*Attorney, Agent, or Firm*—James J. Farrell

[57] ABSTRACT

Plant anti freeze proteins can advantageously be incorporated into frozen confectionery products, provided they have the capability of limiting the growth of ice crystals

9 Claims, No Drawings

SEQUENCE LISTING

```
<160> NUMBER OF SEQ ID NOS: 5

<210> SEQ ID NO 1
<211> LENGTH: 7
<212> TYPE: PRT
<213> ORGANISM: CARROT ROOT

<400> SEQUENCE: 1

Leu Pro Asn Leu Phe Gly Lys
  1               5


<210> SEQ ID NO 2
<211> LENGTH: 9
<212> TYPE: PRT
<213> ORGANISM: CARROT ROOT

<400> SEQUENCE: 2

Ile Pro Glu Glu Ile Ser Ala Leu Lys
  1               5


<210> SEQ ID NO 3
<211> LENGTH: 10
<212> TYPE: PRT
<213> ORGANISM: CARROT ROOT
<220> FEATURE:
<221> NAME/KEY: UNSURE
<222> LOCATION: (3)
<223> OTHER INFORMATION: Xaa represents any amino acid in plant protein

<400> SEQUENCE: 3

Leu Thr Xaa Leu Asp Leu Ser Phe Asn Lys
  1               5                  10


<210> SEQ ID NO 4
<211> LENGTH: 22
<212> TYPE: PRT
<213> ORGANISM: CARROT ROOT
<220> FEATURE:
<221> NAME/KEY: UNSURE
<222> LOCATION: (21)
<223> OTHER INFORMATION: Xaa represents any amino acid found in plant
      protein

<400> SEQUENCE: 4

Ser Leu Arg Leu Ser Ser Thr Ser Leu Ser Gly Pro Val Pro Leu Phe
  1               5                  10                  15

Phe Pro Gln Leu Xaa Lys
             20


<210> SEQ ID NO 5
<211> LENGTH: 16
<212> TYPE: PRT
<213> ORGANISM: CARROT ROOT
<220> FEATURE:
<221> NAME/KEY: UNSURE
```

-continued

```
<222> LOCATION: (1)..(7)
<223> OTHER INFORMATION: Xaa represents any amino acid found in plant
      protein

<400> SEQUENCE: 5

Xaa Xaa Glu Val Ile Pro Xaa Gln Leu Ser Thr Leu Pro Asn Leu Lys
  1               5                  10                  15
```

FROZEN FOOD PRODUCT

TECHNICAL FIELD OF THE INVENTION

The invention relates to frozen food products containing AFPs.

BACKGROUND TO THE INVENTION

Antifreeze proteins have been described in the literature, see for example Marilyn Griffith and K. Vanya Ewart in Biotechnology Advances, Vol 13, No 3, pp 375–402, 1995. Antifreeze proteins generally possess one or more of the following properties: thermal hysteresis, inhibition of ice recrystallisation, control of ice crystal shape and interaction with ice nucleators.

Thermal hysteresis is the best known property of AFPs and the property is normally used to test for the presence of AFPs. Thermal hysteresis results from a lowering of the apparent freezing temperature of a solution containing a thermal hysteresis active AFP without affecting the melting temperature. The identification of sources of AFP by thermal hysteresis tests is widely described in the literature, see for example John G. Duman in Cryobiology 30, 322–328 (1993).

Inhibition of ice recrystallisation is another property of AFPs. This activity is also referred to as ice crystal growth suppression. This property can be tested by comparing at a certain point in time the ice crystal size of crystals in the presence of AFP and in the absence of AFP. The application of this method in the testing of fish AFPs is described in U.S. Pat. No. 5,118,792 (DNA Plant Technology Corporation)

A third property of AFPs is their ability to influence the shape of ice crystals. This property stems from the selective binding of AFPs to certain faces of the ice crystal and therewith limiting crystal growth in certain directions. The presence of ice crystals having an hexagonal bipyramid shape is then considered indicative of the presence of AFP. This method is for example described for testing the activity of extracellular winter rye AFPs in WO 92/22581 (University of Waterloo).

A fourth property of AFPs is their ability to inhibit the activity of ice nucleating substances. This interaction between an AFP and an ice nucleator may for example result in increased thermal hysteresis. This property is for example tested in WO 96/40973 (University of Notre dame du Lac)

AFPs have been suggested for improving the freezing tolerance of products. Many applications have been suggested in this context.

For example AFPs have been suggested for enhancing the cryopreservation of biological materials (WO 91/12718, Agouron Pharmaceuticals, WO 91/10361, The Regents of the University of California). Also AFPs have been suggested to prevent leakage from liposomes e.g. in cosmetic or pharmaceuticals (see WO 96/20695). A further possible application is to increase the freezing tolerance of plants by including therein (or transgenetically producing therein) an AFP (See J. Cell. Biochem. Suppl. vol. 14e, 1990, page 303 XP002030248, Lee et al, abstract R228). Also fish AFPs have been suggested for use in food products for example in frozen yoghurt or ice cream (U.S. Pat. No. 5,620,732 Pillsbury and WO 96/11586, HSC Research and development limited partnership).

Up till now, however the use of AFPs has not been applied on a commercial scale. Applicants are of the opinion that one of the reasons for the lack of commercial implementation is that although many AFPs have been described, in practice the implementation in actual commercial products encounters serious problems.

Applicants have found that one of the key reasons for these problems is that out of the great number of AFPs that have been described in the literature only a limited set of AFPs can suitably be applied for each application; also applicants have found that this selection of suitable AFPs is dependent on the desired application and/or product attributes to be achieved.

A particular desirable source of AFPs is plant material. Plant materials can fairly easily be obtained in relatively large quantities and relatively simple isolation procedures can be used for obtaining an AFP containing concentrate. Furthermore the use of AFPs from plant material is believed to be favoured by consumers who tend to prefer natural vegetable sources to e.g. fish AFPs.

Marilyn Griffith and K. Vanya Ewart in Biotechnology Advances, Vol 13, No 3, pp 375–402, 1995 have given a list of 27 higher plant species in which antifreeze activity is found. This article also suggests a wide range of possible applications for AFPs.

Applicants have now found that if a specific application for the use of plant AFPs is selected, this creates the need for a specific test to select the limited set of AFPs which can advantageously be applied in this application.

The object of the present invention is therefore to provide those plant AFPs which can advantageously be used in frozen confectionery products.

Surprisingly, applicants have found that despite the fact that a great number of plants contain AFPs, only a limited set of plants contains AFPs which are capable of providing a good texture to frozen confectionery products. Surprisingly it has been found that a relatively simple test method can be used to select the suitable AFPs.

Accordingly in a first aspect the invention relates to frozen confectionery products comprising one or more AFPs derived from plants, wherein the AFPs in water have an ice crystal size after quick freezing to −40° C. followed by storage for 1 hour at −6° C. (measured as described below) of less than 15 $\mu$m.

BACKGROUND TO THE INVENTION

A number of literature places have suggested that AFPs may potentially be used for favourably influencing the textural properties of frozen confectionery products such as ice cream. However most of these documents do not provide a teaching how these favourable properties can actually be achieved in practice.

A further set of documents describes the use of fish AFPs.

WO 96/11586 teaches the application of fish antifreeze polypeptides in frozen fermented food products. This document does not teach the use of specific AFPs derived from plants in these products.

WO 96/39878 describes the application of AFP in ice-cream. Suitable AFPs for this application may be derived from blood and muscle tissue of antartic fish, artic fish, worms and insects. Again no teaching is provided that plant AFP can be used.

U.S. Pat. No. 5,118,792 describes in example 3B the inhibition of recrystallisation by a purified A-Saf5 fusion protein in a popsicle mixture. Again this document does not teach the use of AFPs derived from plants.

WO 92/22581 describes a plurality of polypeptides derived from the extracellular spaces of winter rye. Several possible applications of these polypeptides are described in general, among these is ice-cream. However no teaching is provided which of the polypeptides should be selected to obtain a good quality ice-cream. Applicants have found that only specific proteins from winter rye are suitable for use in ice-cream (see examples).

Applicants have found that a great number of plants which up till now have not been listed as such, contain a significant level of AFPs. On the other hand it has been found that not all AFP containing plants provide the right type of AFP for favourably influencing the texture of frozen confectionery. Applicants now aim at providing a particular novel selection of plant sources which surprisingly provide on the one hand good AFP properties and on the other hand are capable of favourably influencing the textural properties of ice cream.

In particular it has been found that suitable AFPs can be selected by taking a composition comprising AFP in an aqueous composition, quick freezing this composition to −40 or less followed by storage for 1 hour at −6° C. Suitable AFPs result in an ice crystal size after storage for 1 hour at these conditions of less than 15 μm, more preferably 5–14 μm, most preferred 8 to 12 μm. The temperature of quick freezing is advantageously −40 to −100° C., preferably −80° C.

A detailed description of a suitable test to determine this characteristic is given in example I.

Generally the test can be applied to any suitable composition comprising AFP and water. Generally the level of AFP in such a test composition is not very critical and can for example be from 0.0001 to 0.5 wt %, more preferred 0.0005 to 0.1 wt %, most preferred 0.001 to 0.05 wt %, for example 0.01 wt %. The water level in the aqueous composition is advantageously 30 wt % or more, for example 50 wt % to 99.9999 wt %

Any suitable composition comprising AFP and water can be used to carry out the test. If desired additives may be present, e.g. sucrose or buffering agents. Generally, however, it will not be necessary to obtain the AFP in purified form. For practical applications normally it would suffice to prepare a liquid extract or juice of plant material, wherein this extract or juice can then be tested. A suitable method to prepare suitable liquid compositions is given in example II.

Normally plants to be tested for suitable AFPs have been subjected to cold. For example plants can be tested which grow in cold climates, for example antartic plants. Alternatively plants can be harvested during the winter period, preferably December to March, more preferred January to February, most preferred in January (northern hemisphere) or June to September, more preferred July to August, most preferred July (southern hemisphere).

Applicants have subjected a great number of plants to the above described test. The results are given in examples III and IV.

Preferred sources of AFPs are derived from *Polystichum mohriodes, Ranunculus biternatus, Nothofagus antartica, Cerastium fontanum, Colobanthus quitensis, Rumex acetosella, Salix fragilis, Calluna vulgaris, Aceana magellanica, Pisum sativum, Acer saccheraroides,* Oxalis, Geranium, *Daucus carota* (carrot), *Vinca minor* (periwinkle), *Vinca major,* Polemonium, Buddleia, Forsythia, *Sambucus nigra, Juncus squarrosus, Carex aquatilis, Agrostis tenuis, Deschampsia antartica, Festuca contracta, Festuca rubra, Parodiochloa flabellata, Phleum alpinum, Poa annua* (speargrass), *Poa pratensis* (Kentucky blue grass), *Rostkovia magellanica,* Bambosoideae, *Chorisodontium aciphyllum, Drepanocladus uncinatus, Isothenicium myosuriodes, Polytrichum alpestre, Alectoria nigricans, Caloplaca regalis, Himantormia lugubris, Hypogymnia physodes, Parmelia subrudecta, Ramalina farinaceae, Stereocaulon glabrum, Umbilicaria antartica, Usnea subfloridana, Poa trivialis, Lolium perenne, Holcus lanatus, Bromus sterilis* and *Festuca contracta.*

Applicants are of the opinion that based on the guidelines given in the description of the invention the skilled person will be well able to select further AFPs which can suitably be derived from plants. The use of these AFPs is also embraced within the scope of the present invention.

In one embodiment particularly useful for application in food products are those plant AFP, which satisfy the above defined crystal size test and which are derived from non- or low-toxic plants. In this context preferred are AFP derived from carrots, grasses, bamboo etc.

Another preferred selection from the above sources is the AFPs derived from the Lichen family, in particular *Alectoria nigricans, Caloplaca regalis, Himantormia lugubris, Hypogymnia physodes, Parmelia subrudecta, Ramalina farinaceae, Stereocaulon glabrum, Umbilicaria antartica, Usnea subfloridana.* These AFPs show particularly good properties in frozen confectionery products.

Other AFPs which show particularly good activity are derived from *Juncus squarrosus* or Geranium.

For some applications those AFPs are selected which maintain their ability to limit ice crystal growth (as evidenced by the above test) even after heat treatment above a temperature of 60° C., most preferably from 80 to 105° C. for a period of at least 30 seconds, more preferred more than 1 minute, 10 minutes or even more than 1 hour. Suitable plant sources which are heat stable are for example *Acer saccharoides,* Bamboo, Buddleia, *Isothecium myosuroides, Ramalina farinaceae, Usnea subfloridana,* Forsythia, Oxalis, *Poa trivialis, Lolium perenne, Holcus lanatus, Bromus sterilis, Parodiochloa flabellata, Deschampsia antartica, Carex aquatilis, Colobanthus quintensis* and *Agrostis tenuis, Festuca contracta, Poa annua.*

In addition to the plants mentioned above applicants have tested the AFPs from *Secale cereale* (winter rye). Several winter rye AFPs have been described in WO 92/22581. Surprisingly applicants have found that the 32 kDa protein derived from winter rye satisfies the above described crystal size test, while other proteins from winter rye do not satisfy the test (see example IX.) For the purpose of the invention, therefore if AFPs derived from winter rye are used, preferably the 32 kDa protein is applied.

Another preferred embodiment of the invention relates to the use in frozen confectionery products of plant AFPs which satisfy the above test and which are not derived from winter rye.

DETAILED DESCRIPTION OF THE INVENTION

Frozen products in accordance to the present invention comprise at least one AFP, which can be derived from plant sources.

The AFPs can be obtained from the plant sources by any suitable process, for example the isolation processes as described in the above mentioned documents. Alternatively the AFPs can be extracted from the plants, for example by preparing a plant extract from (parts) of the plant followed by an optional concentrating step. Examples of suitable methods for obtaining said extracts are given in the examples.

Also microorganisms or plants may be genetically modified to express AFPs and the AFPs may then be used in accordance to the present invention.

Genetic manipulation techniques may be used to produce AFPs having at least 80%, more preferred more than 95%, most preferred 100% homology to the AFPs directly obtained from plant sources which naturally contain the AFPs. For the purpose of the invention these AFPs possessing this high level of homology are also embraced within the term "AFP derived from plants". For the purpose of the invention the term "AFP derived from plants" preferably does not include AFPs which naturally occur in non-plant sources e.g. fish and which by transgenetic routes are produced by plants.

The genetic manipulation techniques may be used as follows: An appropriate host cell or organism would be transformed by a gene construct that contains the coding region for the desired polypeptide.

The nucleotide sequence coding for the polypeptide can be inserted into a suitable expression vector. Said vector encoding the necessary elements for transcription and translation, and in such a manner that they will be expressed under appropriate conditions (e.g. in proper orientation and correct reading frame and with appropriate targeting and expression sequences).

The methods required to construct these expression vectors are well known to those skilled in the art.

A number of expression systems may be utilised to express the polypeptide coding sequence. These include, but are not limited to, bacteria, yeast, insect cell systems, plant cell culture systems and plants all transformed with the appropriate expression vectors.

AFPs obtainable from the above mentioned sources can be used in any suitable frozen confectionery product. For the purpose of the invention the term frozen confectionery product includes milk containing frozen confections such as ice-cream, frozen yoghurt, sherbet, sorbet, ice milk and frozen custard, water-ices, granitas and frozen fruit purees. For some purposes the use in fermented frozen food products is less preferred.

Preferably the level of AFPs in the frozen confectionery product is from 0.0001 to 0.5 wt % based on the final product, more preferred 0.0005 to 0.3 wt %, most preferred 0.001 to 0.2 wt %.

Preferably the level of solids in the frozen confection (e.g. sugar, fat, flavouring etc) is more than 2 wt %, more preferred from 4 to 70 wt %.

If desired the frozen confectionery products of the invention may be aerated, for example to an overrun of from 50 to 500%.

The method of preparing the frozen confectionery product of the invention can be selected from any suitable method for the preparation. The AFPs can generally be added at various stages of the preparation, for example it can be added in the first pre-mix of ingredients or can later be added during a later stage of the preparation process. For some applications it is sometimes preferred to add the AFPs at a relatively late stage of the production process, for example after (partial) pre-freezing of the product.

The freezing process for frozen confectionery products can be selected from any suitable freezing process and may optionally comprise an aeration step for example to an overrun of 50 to 300%. For some purposes it is advantageous that the freezing process involves a cold hardening step, for example at a temperature of −30 Fahrenheit or lower.

For some applications it may be advantageous to include a mixture of two or more different AFPs into the frozen confectionery product. One reason for this can for example be that the plant source for the AFP's to be used, contains more than one AFP and it is more convenient to add these, for example because they are both present in the plant extract to be used. Alternatively it may sometimes be desirable to add more than one AFP from different sources.

The invention will now be illustrated by means of the following examples

EXAMPLE I

Test for Determining Ice Crystal Particle Size After Quick Cooling Followed by Storage at −6° C. for 1 Hour The preferred method is as follows:

Ia: Anti-freeze activity was measured using a modified "splat assay" (Knight et al, 1988). 2.5 $\mu$l of the solution under investigation in 30% (w/w) sucrose was transferred onto a clean, appropriately labelled, 16 mm circular coverslip. A second coverslip was placed on top of the drop of solution and the sandwich pressed together between finger and thumb. The sandwich was dropped into a bath of hexane held at −80° C. in a box of dry ice. When all sandwiches had been prepared, sandwiches were transferred from the −80° C. hexane bath to the viewing chamber containing hexane held at −6° C. using forceps pre-cooled in the dry ice. Upon transfer to −6° C., sandwiches could be seen to change from a transparent to an opaque appearance. Images were recorded by video camera and grabbed into an image analysis system (LUCIA, Nikon) using a 20× objective. Images of each splat were recorded at time=0 and again after 60 minutes.

Alternatively (less preferred) the properties can be measured as follows:

Ib: A sample of an AFP containing product containing water is adjusted to a sucrose level of 30 wt % (If the starting level of the sample is more than 30% this was done by dilution, if the starting level was lower sucrose was added to the 30% level).

A 3 $\mu$L drop of the sample is placed on a 22 mm coverslip. A 16 mm diameter cover-slip is then placed on top and a 200 g weight is placed on the sample to ensure a uniform slide thickness. The edges of the coverslip are sealed with clear nail varnish.

The slide is placed on a Linkham THM 600 temperature controlled microscope stage. The stage is cooled rapidly (50° C. per minute) to −40° C. to produce a large population of small crystals. The stage temperature is then raised rapidly (50° C. per minute) to −6° C. and held at this temperature.

The ice-phase is observed at −6° C. using a Leica Aristoplan microscope. Polarised light conditions in conjunction with a lambda plate were used to enhance the contrast of the ice-crystals. The state of the ice phase (size of ice-crystals) is recorded by 35 mm photomicrography at T=0 and T=1 hour. Whereby an average particle size (visual determination, number average) of below 15 $\mu$m indicates a suitable AFP for use in frozen confectionery products.

EXAMPLE II

Methods to obtain compositions containing AFP and water.

A. Fresh tissue of plant parts, for example roots, stems, buds or leaves can ground with a pestle and mortar (cooled to 4° C.) in an equal volume buffer A (for example 10 mM EDTA, 20 mM Ascorbic acid, buffered with Tris to pH 7.4) held on ice. The homogenates are filtered through one or more layers of muslin and kept on ice prior to further use.

This method can generally be applied to most plants and provide fresh plant juice containing the AFP. Generally the entire plant can be used for this purpose although for practical reasons only parts may sometimes be used (for example leaves from woody trees, roots from root vegetables and stems from grassy plants).

B. Method to extract AFPs from sources which are capable of withstanding heat such as grasses. This method is exemplified by using mixed grass. However it will be apparent that this method may equally be applied to other heat stable sorts.

Mixed grass tissue (*Poa Trivialis, Lolium Perenne, Holcus Lanatus, Bromus Sterilis*) was cut in January (mean temperature in that month was 3.5° C. ensuring the appropriate cold acclimatization of the plants). The grass tissue was rapidly transported into the laboratory for further handling and washed thoroughly with water to remove dirt.

500 g of grass clippings was placed in a 650 Watt microwave oven and heated at full power for 5 minutes, whereby the temperature was raised to 85 to 100° C. The grass clippings were then cooled to ambient temperature.

After the heating step the AFP rich juice was separated from the clippings by filtering. The mass was stirred continuously for 5 minutes in the presence of an equal volume of water and then squeezed through 3 layers of muslin.

EXAMPLE III

Screening of various plants. Non antarctic plants were harvested in January (mid winter). The antarctic plants were harvested mid summer (February-March).

Unless indicated otherwise roots were used to prepare an AFP containing juice according to the method as decribed in example IIa.

The samples were subjected to the test of Example Ia. Suitable AFPs for application in frozen confectionery products are indicated with a positive sign (+).

Additionally the thermal hysteresis properties of the juices was measured as follows: The thermal hysteresis of a sample of a product containing AFPs was determined by placing the melted product on a microslide (Camlab Cambridge, path length 0.1 mm). The ends of the microslide are sealed with petroleum jelly. Ice is introduced into the sample using an aerosol freezing spray. The slide was then immersed in ethanol temperature regulated bath at −0.1° C. After 5 minute equilibration the sample is checked. if the ice melts completely the temperature of the bath was lowered in 0.1° C. steps followed by equilibration. These steps are repeated until a temperature was reached where a small amount of ice crystals exist in the sample. After equilibration at that temperature, the bath temperature was decreased in steps of 0.01° C. per minute. The freezing point of the sample is recorded as the temperature at which the ice propagation begins from the equilibrated crystals. The melting temperature of the sample is then determined by raising the temperature starting at the freezing point in steps of 0.01° C. per minute until all ice-crystals melt. This temperature is the melting temperature of the sample. The thermal hysteresis of the sample is the difference between the melting temperature and the freezing temperature. AFPs with a significant degree of thermal hysteresis are indicated with a positive sign (+). The following results are obtained:

| Plant name | Thermal Hysteresis | Recrystallisation inhibition (Ex I) |
|---|---|---|
| Equisitum hymenale | + | − |
| Picea glauca | + | − |
| Dicentra cucularia | + | − |
| Viola sp. | + | − |
| Brassica oleracea | + | − |
| Brassica rapa | + | − |
| Brassica napus | + | − |
| Daucus carota | + | + |
| Vinca minor | + | + |
| Solanum tuberosum | + | − |
| Poa annua | + | − |
| Poa pratensis | + | − |
| Secale cereale | + | *) |
| Petroselinum crispum | + | − |
| Salvia officinales | + | − |

*) Note: active but only the 29–32 kDa protein

These results clearly show that although a great number of plants show thermal hysteresis properties, only a small proportion of these satisfy the recrystallisation test.

EXAMPLE IV

Screening of various plants. Non antarctic plants were harvested in January (mid winter). The antarctic plants were harvested mid summer (February-March).

Unless indicated otherwise roots were used to prepare an AFP containing juice according to the method as decribed in example IIa.

The samples were subjected to the test of Example Ia. Suitable AFPs for application in frozen confectionery products are indicated with a positive sign (+)

| PLANT NAME | RI test |
|---|---|
| Water horsetail | − |
| Asplenium scolopendrium | − |
| Polystichum mohriodes | + |
| Pinus sylvestris | − |
| Picea glauca | − |
| Cupress sp | − |
| Laurus | − |
| Ranunculus biternatus | + |
| Dicentra | − |
| Platanus orientalis | − |
| Urtica | − |
| Pterocarya fraxinifolia | − |
| Nothofagus antarctica | + |
| Nothofagus oblique | − |
| Betula pendula | − |
| Beta vulgaris | − |
| Cerastium fontanum | + |
| Colobanthus quitensis (pearlwort) | + |
| Rumex acetosella | + |
| Paeonia | − |
| Hypericum | − |
| Alcea | − |
| Viola | − |
| Populus alba | − |
| Salix alba 'Britzensis' | − |
| Salix daphnoides | − |
| Salix fragilis | + |
| Sorbus aria | − |
| Prassica napus | − |
| Erysimum | − |
| Calluna vulgaris | + |
| Primula | − |

-continued

| PLANT NAME | RI test |
|---|---|
| Hydrangea | |
| Sedum | − |
| Acaena magellanica | + |
| Crategus monogyna | − |
| Cotoneaster spp x2 | − |
| Fragaria x ananassa | − |
| Alchemilla | − |
| Cytisus | − |
| Pisum sativum | + |
| Vicia faba | − |
| Medicago sativa | − |
| Daphne | − |
| Eucalyptus | − |
| Aucuba | − |
| llex | − |
| Acer saccharoides | + |
| Rhus | − |
| Oxalis | + |
| Geranium | + |
| Hedera | − |
| Daucus carota | + |
| Pastinaca sativa | − |
| Vinca | + |
| Polemonium | + |
| Rosmarinus | − |
| Buddleia | + |
| Forsythia | + |
| Fraxinus ornus | − |
| Lonicera pileata | − |
| Sambucus nigra | + |
| Lactuca sativa | − |
| Tragopodon porrifolius | − |
| Helianthus tuberosus | − |
| Juncus squarrosus | + |
| Carex aquatilis | + |
| Agrostis tenuis | + |
| Deschampsia antarctica | + |
| Festuca contracta | + |
| Festuca rubra | + |
| Parodiochloa flabellata | + |
| Phleum alpinum | + |
| Poa annua | + |
| Poa pratensis | + |
| Rostkovia magellanica (grass) | + |
| Bambosoideae sp | + |
| Muscari armenicum | − |
| Allium ampeloprasum cv Alaska | − |
| Allium cepa | − |
| Chorisodontium aciphyllum | + |
| Drepanocladus uncinatus | + |
| Isothecium myosuroides | + |
| Neckera complanata | − |
| Polystichum alpestre | + |
| Polytrichum commune | − |
| Polytrichum formosum | − |
| Racometrium lanuginosum | − |
| Sphagnum capillofolium | − |
| Sphagnum palustre | − |
| Alectoria nigricans | + |
| Caloplaca regalis | + |
| Himantormia lugubris | + |
| Hypogymnia physodes | + |
| Parmelia subrudecta | + |
| Ramalina farinaceae | + |
| Stereocaulon glabrum | + |
| Umbilicaria antarctica | + |
| Usnea subfloridana | + |

EXAMPLE V

A liquid pre-mix for preparing ice-cream was made by mixing:

| Ingredient | % by weight |
|---|---|
| Skimmed milk powder | 11.390 |
| Sucrose | 3.410 |
| Maltodextrine (MD40) | 4.000 |
| Locust bean gum | 0.072 |
| Corn Syrup 63DE | 20.705 |
| Guar Gum | 0.048 |
| Genulacta L100 | 0.020 |
| Butter | 9.015 |
| Avicel RC581 | 0.240 |
| Gelatin | 0.140 |
| Monoglyceride (palmitate) | 0.450 |
| Vanillin | 0.010 |
| AFP (of example IIb) | 0.100 or none (control) |
| Water | balance |

*Note: AFP is added as concentrated AFP solution using some of the added water as a diluent, percentage refers to amount of AFP.

This mix can conveniently be pasteurised at 85° C. for 15 seconds and stored chilled in a can.

The mixes can be used in the preparation of a ice-cream by whipping with a conventional house-hold mixer to an overrun of about 100%, followed by quiescently freezing into a house-hold freezer.

The composition according to the invention had a markedly better texture than the control sample.

Similar results can be obtained by using the following plants sources: *Acer saccharoides,* Bamboo, Buddleia, *Isothecium myosuroides, Ramalina farinaceae, Usnea subfloridana,* Forsythia, Oxalis, *Poa trivialis, Lolium perenne, Holcus lanatus, Bromus sterilis, Parodiochloa flabellata, Deschampsia antartica, Carex aquatilis, Colobanthus quintensis* and *Agrostis tenuis, Festuca contracta, Poa annua*

EXAMPLE VI

A liquid premix for the preparation of ice-cream was prepared by mixing:

| Ingredient | % by weight |
|---|---|
| Skimmed milk powder | 10.00 |
| sucrose | 13.00 |
| maltodextrine (MD40) | 4.00 |
| Locust bean gum | 0.14 |
| butteroil | 8.00 |
| monoglyceride (palmitate) | 0.30 |
| vanillin | 0.01 |
| AFP (of example IIb) | 0.01 or none (control) |
| water | balance |

*Note: AFP is added as concentrated AFP solution in some of the water, percentage refers to amount of AFP.

The ingredients were mixed at ambient temperature followed by pasteurisation for 60 seconds at 89° C. The mix was aseptically filled into packs of 500 ml, sealed and stored at ambient temperatures.

The mix can be used for the preparation of ice-cream by whipping it with a conventional house-hold mixer to an overrun of about 70% followed by freezing under quiescent conditions in a house-hold freezer. After two months storage the composition according to the invention had a markedly better texture than the control sample.

EXAMPLE VII

This example describes the isolation and sequencing of carrot AFP. Similar methods can be used for other plant AFPs.

Carrot root tissue of cold acclimatised carrots was homogenized in three volumes (w/v) buffer (20 mM ascorbic acid, 10 mM EDTA, 50 mM Tris/HCL, pH 7.2) in a pre-cooled pestle and mortar and filtered through one layer of muslin. The filtrate was centrifuged at 6,000 g, ten minutes at 4° C.; the supernatant was collected and centrifuged at 100,000 g for 1 hour at 4° C. The 100,000 g supernatant from this step is termed the soluble fraction and the pellet the microsomal fraction.

The supernatant was applied to a 30 ml fast flow Q Sepharose (Pharmacia) column pre-equilibrated in 50 mM Tris/HCL pH 7.4 at a flow rate of 5 ml/min supplied by a HiLoad pump P-50 controlled by a Gradifrac low pressure chromatography system (Pharmacia) at 4° C. and the eluate monitored at OD 280 by a UV monitor (Monitor UV1, Pharmacia) recorded on a chart recorder (REC 102, Pharmacia). 5 ml fractions were collected. The column was washed with 50 mM Tris/HCL pH 7.4 at the same flow rate until the OD 280 returned to zero. A 150 ml gradient of 0–0.4 M NaCl in Tris/HCL pH 7.4 was then applied followed by a 2 M NaCl column wash. Eluate fractions were subjected to the splat assay as in example I.

Fractions containing anti-freeze activity were pooled and concentrated using polyethylene glycol as follows: the fractions were transferred in 10 kDa cut off dialysis tubing (Sigma) which had been washed in tap water, boiled in 50 mM EDTA pH 7.5 for 10 minutes and rinsed in milli Q water. The dialysis tubing containing the sample to be concentrated was covered with solid polyethylene glycol compound Mol. Wt. 15,000–20,000 (Sigma) and incubated at 4° C. for up to 4 hours or until the sample volume inside the dialysis tubing had reduced up to 10 fold.

The pooled concentrate from the Q sepharose column was applied either to a phenyl Sepharose column, a SMART superdex 75 gel permeation column or an FPLC superdex 75 gel permeation column.

Carrot root anti-freeze proteins were purified by gel permeation chromatography as follows:

20 $\mu$l aliquots of sample were applied to a SMART superdex 75 column (Pharmacia) pre-equilibrated in 50 mM Tris/HCl pH7.4 containing 0.15M NaCl (Buffer E) at a flow rate of 40 $\mu$l/min and components separated by gel permeation at the same flow rate in equilibration buffer. The eluate was monitored at OD 280 and OD 215. 80 $\mu$l fractions were collected between 0.85 and 0.89 ml, 40 $\mu$l fractions between 0.89 and 1.24 ml and 100 $\mu$l fractions between 1.24 and 3.0 ml. The void volume (Vo) of the column was 0.91 ml as determined by the retention volume of a solution of Blue Dextran. The superdex column was calibrated by application of 10 $\mu$l of a solution containing 5 mg/ml BSA (Mr 66 kDa, retention (Ve)=1.02 ml), 3 mg/ml Carbonic anhydrase (Mr 29 kDa, Ve=1.22 ml), 2 mg/ml Cytochrome C (Mr 12.4 kDa, Ve=1.41 ml) and 2 mg/ml Aprotinin (Mr 6.5 kDa, Ve=1.59 ml) and a standard curve plotted of Ve/Vo against log Mr. Fractions containing anti-freeze activity were identified by the spat assays in Example I, with an activity peak that showed a retention volume of 1.16 ml and an apparent molecular weight of 40 kDa. These measurement confirmed that the 38 kDa band from cold acclimatised carrots was an anti-freeze peptide.

SDS-PAGE was carried out according to Laemmli (1970) using the Biorad mini system. Samples to be analyzed by SDS-PAGE were dissolved in SDS-PAGE sample buffer (Laemmli 1970), heated for 5 minutes at 100° C. on a dry heating block (Techne) and centrifuged for 3 minutes at 10,000 g at room temperature. Samples (10–50 $\mu$l) were applied to mini-gels (Biorad, 0.75, 1.0 or 1.5 mm thickness, 10, 12, 15% acrylamide or 10–20% gradient acrylamide {pre-poured from Biorad}) and electrophoretically separated. Separated polypeptides were fixed and stained in the gel either with Coomassie blue (0.1% {w/v} Coomassie Brilliant Blue in acetic acid/methanol/miliQ water {5:4:31, by vol}) or silver stained using the Biorad silver stain kit according to the manufacturer's instructions. Gels were dried between two sheets of Gelair collophane in a Biorad gelair dryer according to the manufacturer's instructions. Sigma high and low range molecular weight marker kits were used according to the manufacturer's instructions for determination of apparent $M_r$ on SDS-PAGE.

The ion exchange chromatography was carried out with cold acclimatised carrot root and non-cold acclimatised carrot root. The resulting gel SDS-PAGE gels showed the presence of a about 38 kDa band in the cold acclimatised sample. This band was much less abundant in the non-cold acclimatised root. This (about) 38 kDa band was hence attributed to anti-freeze activity.

For protein sequencing, the carrot root protein of about 38 kDa was purified as described in the previous example and then to ensure further purification the sample to be sequenced was excised from the SDS PAGE gel and then proteolytically digested in situ in the polyacrylamide gel slice.

Preparations of largely pure of protein about 38 kDa, that still had some minor contaminating proteins, were loaded onto a 12% polyacrylamide gel. Three lanes each with 2 $\mu$g of protein were loaded and electrophoresed in the gel until the dye front reached the bottom of the gel. The gel was then stained in 0.2% coomassie brilliant blue (w/v), 30% methanol (v/v), 1% acetic acid (v/v) for 20 minutes and then destained with 30% methanol until the protein bands could be visualised. The 38 kDa band was identified by comparison with molecular weight markers loaded into adjacent lanes and the band from each lane was excised with a scalpel blade, taking care to exclude contaminating bands.

The gel slices were transferred to a clean eppendorf tube and washed twice with 0.5 ml of 50% acetonitrile (v/v), 100 mM Tris/Cl, pH 8.5. The washing removed some of the coomassie stained and also partially dehydrated the gel slices. The gel slices were then removed from the tube and subjected to air drying on the laboratory bench until they had shrunk significantly and started to curl up. They were then transferred back to the eppendorf and rehydrated with firstly, 10 $\mu$l of 100 mM Tris/Cl, pH 8.5 containing 1 $\mu$g of endoproteinase Lys C (Boehringer Mannheim). This is a proteinase that specifically cleaves polypeptide chains on the carboxy terminal side of lysine residues. Further Tris buffer was added to the gel slices until they were fully rehydrated and they were then incubated at 37° C. for 16 hours.

After incubation 1 $\mu$l of trifluoroacetic acid was added to the tube to stop the reaction and then the gel slices were washed twice with 0.3 ml of 60% acetonitrile (v/v), 0.1% TFA (v/v) at 30° C. for 30 minutes. This was to again partially dehydrate the gel slices causing them to shrink and elute the peptides that had been generated. The supernatant was transferred to another clean eppendorf tube and then dried in a centrifugal evaporator for 2 hours until the sample was near dryness and resuspended to a volume of 0.1 ml with 0.1% TFA.

The peptides were then separated by reversed phase HPLC on a Smart micropurification system (Pharmacia). The peptide digest was loaded onto a C18 column (2.1×100 mm) equilibrated in 0.1% TFA (Solvent A) at a flow rate of 0.1 ml min. The column was then eluted with a gradient of 0–70% of Solvent B (90% acetonitrile v/v, 0.085% TFA v/v) over 70 minutes at the same flow rate. The optical density was monitored at 214 nm and individual peptide peaks were collected in the fraction collector by manual stepping. Polypeptides were sequenced by loading onto a model 492 Perkin Elmer protein sequencer using the liquid phase chemistry cycles as recommended by the manufacturer.

Several polypeptide fragments (A–E) were analyzed in the 38 kDa band and had sequences substantially homologous to:

```
(A) LEU-PRO-ASN-LEU-PHE-GLY-LYS                (SEQ ID NO:1)

(B) ILE-PRO-GLU-GLU-ILE-SER-ALA-LEU-           (SEQ ID NO:2)
    LYS

(C) LEU-THR-X-LEU-ASP-LEU-SER-PHE-             (SEQ ID NO:3)
    ASN-LYS

(D) SER-LEU-ARG-LEU-SER-SER-THR-SER-           (SEQ ID NO:4)
    LEU-SER-GLY-PRO-VAL-PRO-LEU-PHE-
    PHE-PRO-GLN-LEU-X-LYS

(E) X-X-GLU-VAL-ILE-PRO-X-GLN-LEU-             (SEQ ID NO:5)
    SER-THR-LEU-PRO-ASN-LEU-LYS
```

Cell cultures for producing anti-freeze proteins were made as follows:

New cell cultures were initiated based on methods described in Gamborg and Wetter 1975, Torres 1989, Dodds and Roberts 1985.

Cold acclimatised Carrot (Autumn King): the surface of the storage root was sterilized firstly by washing with 10% Teepol detergent, followed by scrubbing under running water then rinsing under running water for 15 minutes. Where practicable (on the basis of size) the root was peeled. The root was then aseptically cut into 0.5 cm slices, which were placed in 70% v/v ethanol for 10 minutes with shaking followed by 10% v/v Domestos+2 drops Tween 20 (Sigma) for 25 minutes, also with shaking. Sections were then washed 3× with sterile distilled water. Cylinders of approximately 0.5 cm diameter were cut through the slices using a sterile scalpel, and the remainder cut into 2–3 mm lengths. These tissue discs (explants) were aseptically transferred onto solid MS medium containing 30 g/l sucrose, 10 mg/l indole acetic acid (IAA), 0.1 mg/l kinetin and 8 g/l technical agar, which was contained in 60 ml Sterilin containers. The explants were incubated in the dark at 20° C.

When necessary, the resulting calli were divided into smaller sections, which were plated onto fresh medium. Suspension cultures were then initiated from actively growing callus.

Additionally carrot cell suspension culture lines (NOR and OX6) were obtained from the Department of Biochemistry and Molecular Biology, University of Leeds. 10 ml of these cultures were sub-cultured into 90 ml of fresh Murashige and Skoog medium (Sigma) containing 25 g/l sucrose and 1 mg/l 2,4-D every seven days. Cultures were incubated in an orbital shaking incubator at 150 rpm at 25° C. in the dark.

The NOR culture was cold treated as follows:

18×5 ml 7 d old NOR culture was added to 18×100 ml Erlenmeyer flasks containing 45 ml carrot MS medium. The cultures were incubated at 25° C. as previously described for 4 days, then the incubator temperature reduced to 4° C. Two flasks were removed immediately and the cells and medium harvested as previously described as t=0. The remaining flasks were harvested in duplicate at t=8 h, 1 d, 2 d, 4 d, 7 d, 9 d, 11 d, and 14 d.

The cold acclimation treatment was repeated using larger cultures of both NOR and OX6, which were transferred to 4° C. after 4 d and 7 d of growth at 25° C. Cultures were harvested at t=0, t=7 d and t=14 d. In addition to harvesting, the PCV was determined for each culture at each time point.

The NOR cold acclimated cells were prepared for splat analysis as in Example I as follows: Quick frozen cells were ground to a fine powder in liquid nitrogen using a pestle and mortar. The powdered samples were resuspended in 2× volume of 10 mM EDTA+20 mM ascorbic acid, whirlimixed for 30 seconds then centrifuged at 10.000 g for 10 minutes. 10 μl aliquots of the supernatants were splatted using the buffer control as a negative control. RI activity could be detected in cold acclimated cells and medium but not in the non-cold acclimated samples.

The media samples from NOR suspension were analyzed as follows. The NOR carrot medium was buffered by addition of 100 μl of 1M Tris/HCl pH 7.4. This was then applied to the 1 ml Q Sepharose column (Pharmacia) at a flow rate of 1 ml/min and bound molecules eluted with 3 ml aliquots of 50 mM Tris/HCl pH 7.4 containing concentrations of 0.5 M NaCl. 1 ml fractions were collected.

This anion exchange method was also used to fractionate t=0, 2 d, 4 d, 7 d, 11 d, cold acclimated and t=7 d non-cold acclimated medium samples. Fractions were tested for activity by sandwich splat assay as described in example I.

The antifreeze activity in culture medium was purified by gel permeation chromatography as follows. The 14 cold acclimated 0.5M NaCl eluate from the Q sepharose column (fraction 2) from above was acetone precipitated and the pellet resuspended in 50 μl 50 mM Tris/HCl+0.15 M NaCl, pH 7.2. This was then centrifuged at 10.000 g for 10 minutes, and 20 μl loaded onto a Superdex 75 gel permeation column on the Pharmacia SMART system. The flow rate was 40 μl/min and the mobile phase was 50 mM Tris/HCl+0.15M NaCl, pH 7.2. 80 μl fractions were collected and splatted. This procedure was repeated using t=14 d non-cold acclimated 0.5M NaCl eluate from the Q sepharose column and fresh medium.

Further isolation of the active proteins can be done by SDS PAGE analysis as described above.

EXAMPLE VIII

Root extract from cold acclimatised carrot roots was prepared by scrubbing freshly pulled cold acclimatised carrots in cold water. The tops are removed and the juice extracted employing a domestic juice extractor (Russell Hobbs, model no 9915). The juice was frozen in 1 liter blocks and stored a −20° C. prior to collection for use in ice cream trials.

The carrot AFP juice was added to the following ice cream formulation

| INGREDIENT | parts by weight |
|---|---|
| Skimmed Milk Powder | 10.000 |
| Sucrose | 13.000 |

-continued

| INGREDIENT | parts by weight |
|---|---|
| MD40 | 4.000 |
| Locust Bean Gum | 0.144 |
| Genulacta L100 | 0.016 |
| MGP | 0.300 |
| Butteroil | 8.000 |
| Vanillin | 0.012 |
| Water | 64.528 |
| *Carrot Extract (from cold acclimated carrots containing 1–10 mg AFP per kg) | 4.472 |

Ice-cream was prepared by freezing above formulation and aeration to 106% overrun.

Measurements were made on fresh sample and on samples which had been abused by storage at −10° C. for a period of 10 days.

As a comparison a sample without carrot extract was measured in the same way. The measurements were done as follows:

Samples were equilibrated at −18 C. in a Prolan Environmental cabinet for approximately 12 hours. Three samples were chosen representatively from each batch of ice cream and a slide was prepared from each in a Cryostat temperature control cabinet by smearing a thin layer of ice cream from the centre of each block onto a microscopic slide. A single drop of white spirit was applied to the slide and a cover slip was then applied. Each slide, in turn, was then transferred to a temperature controlled microscope stage (Leit LaborLux S, Leica x10 objective, temperature −18° C.). Images of ice-crystals (about 400 individual ice-crystals) were collected and relayed through a video camera (Sanyo CCD) to an image storage and analysis system (LEICA Q520MC).

The stored ice crystal images were highlighted manually by drawing around the perimeter which then highlights the whole crystal. Images of the highlighted crystals were then measured using the image analysis software which counts the number of pixels required to complete the longest straight line (length), shortest straight line (breadth), the aspect ratio (length/breadth). The data for each individual ice crystal of a batch of ice cream was imported into a spreadsheet where analysis of the data set was carried out to find the mean, and standard deviation.

The ice Cream Hardness Measurements were carried out using a Hounsfield H10KM Universal Tester, a Hounsfield 100N Load Cell and a 10 cm Cylindrical Stainless steel probe. The ice-cream samples were prepared by 16 Hour incubation of 486 ml ice cream blocks in a Prolan Temperature Control Cabinet set at −18° C.

The ice cream block was removed from Prolan temperature control cabinet and placed the Hounsfield H10KM Universal Tester. The 10 cm cylindrical probe was pushed into the ice cream block at a constant rate of 400 mm/min to a depth of 20 mm. The maximum force recorded during the compression was used and expressed as the ice cream Hardness. If cracking or brittle fracture of the sample was observed this was indicated in the right hand column The following results were obtained

| | Ice Crystal Size Parameters | | | | Material Properties | |
|---|---|---|---|---|---|---|
| Sample | Mean Crystal Length/ um | Mean Crystal Breadth/ um | Mean Crystal Shape Factor/ – | Mean Crystal Aspect Ratio/ – | Hardness/ N | Brittle Fracture observation |
| Carrot AFP - fresh | 26.79 ± 1.3 | 19.00 ± 0.9 | 1.15 ± 0.013 | 1.43 ± 0.024 | 40.8 | Yes |
| Carrot AFP - Abused | 33.48 ± 1.3 | 24.61 ± 0.9 | 1.13 ± 0.013 | 1.37 ± 0.020 | 59.9 | Yes |
| Cont. - Fresh | 33.67 ± 1.1 | 24.79 ± 0.8 | 1.12 ± 0.008 | 1.38 ± 0.018 | 27.3 | No |
| Cont. - Abused | 61.7 ± 2.7 | 46.54 ± 2.0 | 1.11 ± 0.010 | 1.37 ± 0.020 | 32.7 | No |

The following conclusions can be drawn:

a) Initial ice crystal size is smaller in ice cream containing Carrot AFP, thus carrot AFP is inhibiting recrystallization inhibition.

b) Ice crystals in carrot AFP ice cream are retarded in their recrystallization processes.

c) Ice crystal shape in carrot AFP ice creams are not significantly different from crystal shapes seen in conventional ice creams.

d) Material properties of ice cream containing carrot AFP are modified from those noted for conventional ice cream. Namely, ice creams are harder than conventional ice cream but still softer than ice-cream containing e.g. fish AFPs. Secondly, ice cream containing carrot AFP was observed to fracture.

Similarly very good results can be obtained by using Geranium or *Juncus squarrosus.*

EXAMPLE IX

This example describes the isolation of various proteins from winter rye and the testing thereof.

The leaves from 30 days cold acclimated rye plants were cut into 3 cm lengths and thororughly washed in distilled water to remove any cell contents. The leaf pieces were patted dry on paper towel and totally imersed in an extraction medium of 5 mM EDTA, 10 mM ascorbic acid, 2 mM caproic acid, 2 mM benzamidine and 1 mM Phenylmethylsulphonyl Fluoride (PMSF). They were then vacuum infiltrated in a Buchner flask for 60 minutes after which time the leaves were removed and patted completely dry. They were then arranged lengthways is a cut off plastic syringe barrel and centrifuged gently at 2000×g for 30 minutes. The apoplastic extract was collected in an eppendorf tube below the syringe.

The apoplastic extract was concentrated 7 times using and Amicon ultrafilter with a PM10 membrane. Initial purification was performed by loading 50 microliter of concentrated apoplastic extract onto a size exclusion. Superdex 75 PC 3.2/3.0 (separation range 3–70 kDa) column on a SMART separation system, both from Pharmacia. The buffer was 50 mM Tris/HCl at pH 9.5. Separation was carried out at a flow rate of 50 microliter per minute and 50 microliter fractions were collected up to a volume of 2.5 ml and assayed for recrystallisation as described in example I.

Active fractions were loaded onto a strong anion exchange MonoQ FPLC column from Pharmacia, equilibrated in 50 mM Tris/HCl at pH 9.5, and the proteins were eluted using the same buffer with an linear gradient to 0.5 M NaCl. The elution buffer was added to a concentration of 0.5 M NaCl over 25 minutes, held for 10 minutes and reduce to 0 M over 15 minutes. Chromotography was carried out at a flow rate of 1 ml per minute and 1 ml fractions were collected. The fractions which were positive in the test according to example I were concentrated on a Centrican PM10 centrifugal concentrator at 7000 rps until the volume was reduced to 50 microliter and loaded for a second time onto the S75 column. The fraction which satisfied the test of example i was a single peakd at approximately 150 mM salt.

This active fraction was separated on SDS PAGE (similar metodology as in example VII). This confirmed that the 32 kDa was the active fraction.

The 32 kDa fraction of winter rye protein can advantageously be used in the preparation of frozen confectionery products.

What is claimed is:

1. A frozen confectionery products comprising one or more AFPs derived from plants, wherein the AFPs in an aqueous composition have an ice crystal size after quick freezing to −40° C. or less, followed by storage for 1 hour at −6° C. of less than 15 μm.

2. A frozen confectionery product of claim 1, wherein the AFP is derived from *Polystichum mohriodes, Ranunculus biternatus, Nothofagus antartica, Cerastium fontanum, Colobanthus quitensis, Rumex acetosella, Salix fragilis, Calluna vulgaris, Aceana magellanica, Pisum sativum, Acer saccharoides,* Oxalis, Geranium, *Daucus carota* (carrot), *Vinca minor* (periwinkle), *Vinca major,* Polemonium, Buddleia, Forsythia, *Sambucus nigra, Juncus squarrosus, Carex aquatilis, Agrostis tenuis, Deschampsia antartica, Festuca contracta, Festuca rubra, Parodiochloa flabellata, Phleum alpinum, Poa annua* (speargrass), *Poa pratensis* (Kentucky blue grass), *Rostkovia magellanica,* Bambosoideae, *Chorisodontium aciphyllum, Drepanocladus uncinatus, Isothenicium myosuriodes, Polytrichum alpestre, Alectoria nigricans, Caloplaca regalis, Himantormia lugubris, Hypogymnia physodes, Parmelia subrudecta, Ramalina farinaceae, Stereocaulon glabrum, Umbilicaria antartica, Usnea subfloridana, Poa trivialis, Lolium perenne, Holcus lanatus, Bromus sterilis* and *Festuca contracta.*

3. Frozen confectionery product according to claim 2, wherein the AFP is derived from the Lichen family, in particular *Alectoria nigricans, Caloplaca regalis, Himantormia lugubris, Hypogymnia physodes, Parmelia subrudecta, Ramalina farinaceae, Stereocaulon glabrum, Umbilicaria antartica, Usnea subfloridana.*

4. Frozen confectionery product according to claim 2, wherein the AFP is derived from *Juncus squarrosus* or Geranium.

5. Frozen confectionery product according to claim 2, wherein the AFP maintain their ability to limit ice crystal growth after heat treatment above a temperature of 60° C. for a period of at least 30 seconds, more preferred more than 1 minute.

6. Frozen confectionery product according to claim 5 wherein the AFP is derived from *Acer saccharoides,* Bamboo, Buddleia, *Isothecium myosuroides, Ramalina farinaceae, Usnea subfloridana,* Forsythia, Oxalis, *Poa trivialis, Lolium perenne, Holcus lanatus, Bromus sterilis, Parodiochloa flabellata, Deschampsia antartica, Carex aquatilis, Colobanthus quintensis* and *Agrostis tenuis, Festuca contracta, Poa annua.*

7. Frozen confectionery product according to claim 1, wherein the AFP is derived from a non-toxic plant.

8. Frozen confectionery product according to claim 2, wherein the AFP is the 32 kDa protein derived from winter rye.

9. Frozen confectionery product according to claim 2, wherein the product is substantially free from AFPs from winter rye.

* * * * *